(12) United States Patent
Dimitriu et al.

(10) Patent No.: US 6,361,542 B1
(45) Date of Patent: Mar. 26, 2002

(54) OBSTETRICAL VACUUM EXTRACTOR CUP WITH FORCE MEASURING CAPABILITIES

(75) Inventors: Dan G. Dimitriu; Merle M. Smith, both of San Antonio, TX (US)

(73) Assignee: Prism Enterprises, Inc., San Antonio, TX (US)

(*) Notice: Subject to any disclaimer, the term of this patent is extended or adjusted under 35 U.S.C. 154(b) by 0 days.

(21) Appl. No.: 09/573,092

(22) Filed: May 17, 2000

(51) Int. Cl.[7] .............................................. A61B 17/42
(52) U.S. Cl. ........................ 606/123; 606/119; 606/121
(58) Field of Search ................................. 606/121–127, 606/119, 205; 600/561, 587, 595; 73/865.541, 862.621, 862.629; 604/74, 149, 902

(56) References Cited

U.S. PATENT DOCUMENTS

| | | |
|---|---|---|
| 667,447 A | 2/1901 | Miller |
| 897,289 A | 9/1908 | Howell |
| 1,758,962 A | 5/1930 | Miller |
| 2,066,773 A | 1/1937 | Felice |
| 2,194,989 A | 3/1940 | Torpin |
| 2,227,673 A | 1/1941 | Price |
| 2,542,505 A * | 2/1951 | Gascoigne .................. 606/123 |
| 2,702,038 A | 2/1955 | Uddenberg et al. |
| 3,202,152 A * | 8/1965 | Wood et al. ................. 606/123 |
| 3,642,006 A | 2/1972 | Wobbe |
| 3,765,408 A | 10/1973 | Kawai |
| 3,794,044 A | 2/1974 | Vennard et al. |
| 3,988,793 A | 11/1976 | Abitbol |
| 4,014,344 A * | 3/1977 | Gutierrez .................... 606/123 |
| 4,127,632 A | 11/1978 | Anger |
| 4,375,948 A | 3/1983 | von Holdt |
| 4,512,347 A | 4/1985 | Uddenberg |
| 4,620,544 A | 11/1986 | O'Neil |
| 4,633,865 A | 1/1987 | Hengstberger et al. |
| 4,730,617 A | 3/1988 | King |
| 4,794,915 A | 1/1989 | Larsson |
| 4,799,922 A | 1/1989 | Beer et al. |
| 4,995,401 A * | 2/1991 | Bunegin et al. ............. 606/123 |
| 5,019,086 A * | 5/1991 | Neward ....................... 606/123 |
| D320,855 S | 10/1991 | Smith et al. |

(List continued on next page.)

FOREIGN PATENT DOCUMENTS

| | | |
|---|---|---|
| DE | 3535-055 A | 10/1985 |
| SU | 839518 | 6/1981 |
| WO | WO/8906112 | 7/1989 |

OTHER PUBLICATIONS

O'Grady et al., "Vacuum Extraction in Modern Obstetric Practice," pp. 13–21 (The Parthenon Publishing Group, Inc., New York, NY 1995).

(List continued on next page.)

Primary Examiner—Pedro Philogene
(74) Attorney, Agent, or Firm—Leydig, Voit & Mayer, Ltd.

(57) ABSTRACT

An optical strain gauge is coupled to an obstetrical vacuum extractor to measure the tensile strain resulting from the application of an extraction force. The measured strain is transmitted to a readout device and converted to a readable indication of the force applied. The optical strain gauge may be of any suitable design, so long as the measured reading may be transmitted and converted to a readable indication of the applied force either before or at the readout device. Preferably, the strain gauge is connected with an optical fiber to the readout device. The strain gauge may be coupled to or molded to any portion of the extractor that exhibits a tensile or compressive force or bending as a result of the application of the extraction force. In the currently preferred design wherein a stem with a handle is coupled to the cup, a sensor is disposed about the stem between a flange on the stem and the handle, which is moveable along the stem, such that the sensor measures the compressive force between the handle and the flange.

21 Claims, 2 Drawing Sheets

U.S. PATENT DOCUMENTS

| | | | |
|---|---|---|---|
| 5,163,944 A | | 11/1992 | Neward |
| 5,224,947 A | | 7/1993 | Cooper et al. |
| 5,281,229 A | | 1/1994 | Neward |
| 5,308,321 A | * | 5/1994 | Castro .......................... 604/74 |
| 5,395,379 A | | 3/1995 | Deutchman et al. |
| 5,507,752 A | | 4/1996 | Elliott |
| 5,569,265 A | | 10/1996 | Elliott |
| 5,649,934 A | * | 7/1997 | Smeltzer, III et al. ...... 606/122 |
| 5,693,058 A | | 12/1997 | Cavanagh et al. |
| 5,713,909 A | | 2/1998 | Lindsay |
| 5,803,926 A | | 9/1998 | Neward |
| 5,810,840 A | | 9/1998 | Lindsay |
| 5,935,136 A | | 8/1999 | Hulse et al. |
| 5,957,931 A | | 9/1999 | Dimitriu |

OTHER PUBLICATIONS

Vacca, *Handbook of Vacuum Extraction in Obstetric Practice*, pp. 1–12 (Edward Arnold, London, 1992).

J. A. Chalmers, *The Ventouse*, pp. 1–17 (Lloyd–Luke Medical Books 1971).

V. Finderle, "Assisting Delivery Though the Use of an Extractor" *Gynaecologia*, vol. 133, No. 4, pp. 225–30 (Apr. 1952) Foreign language document—translation attached.

V. Finderle, "Extractor Instead of Forceps", *Am. J. Obst & Gynec.*, vol. 69, No. 5, pp. 1148–53 (May 1955).

Svenningsen et al., "Neonatal Retinal Hemorrhages and Nurobehavior Related to Tractive Force in Vacuum Extraction", *Acta Obstet Gynecol Scand.*, vol. 66, pp. 165–169 (1987).

Moolgaoker et al., "A Comparison of Different Methods of Instrumental Delivery Based on Electronic Measurements of Compression and Traction", *Obstetrics and Gynceology*, vol. 54, No. 3, pp. 299–309 (Sep. 1979).

Saling et al. "Equipment for the Recording of Tractive Power in Vacuum Extractions", *J. Perinat. Med.*, vol. 1, pp. 142–144 (1973).

Svenningsen, "Birth Progression and Traction Forces Developed Under Vacuum Extraction After Slow or Rapid Application of Suction", *Eur. J. Obstet. Gynecol. Reprod. Biol.*, vol. 26, pp. 105–112 (1987).

* cited by examiner

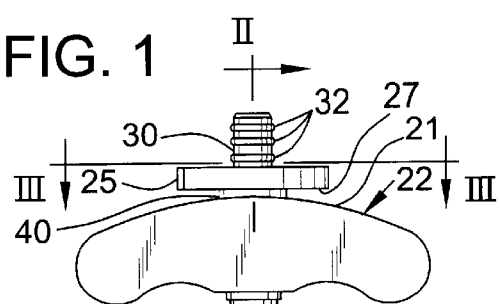
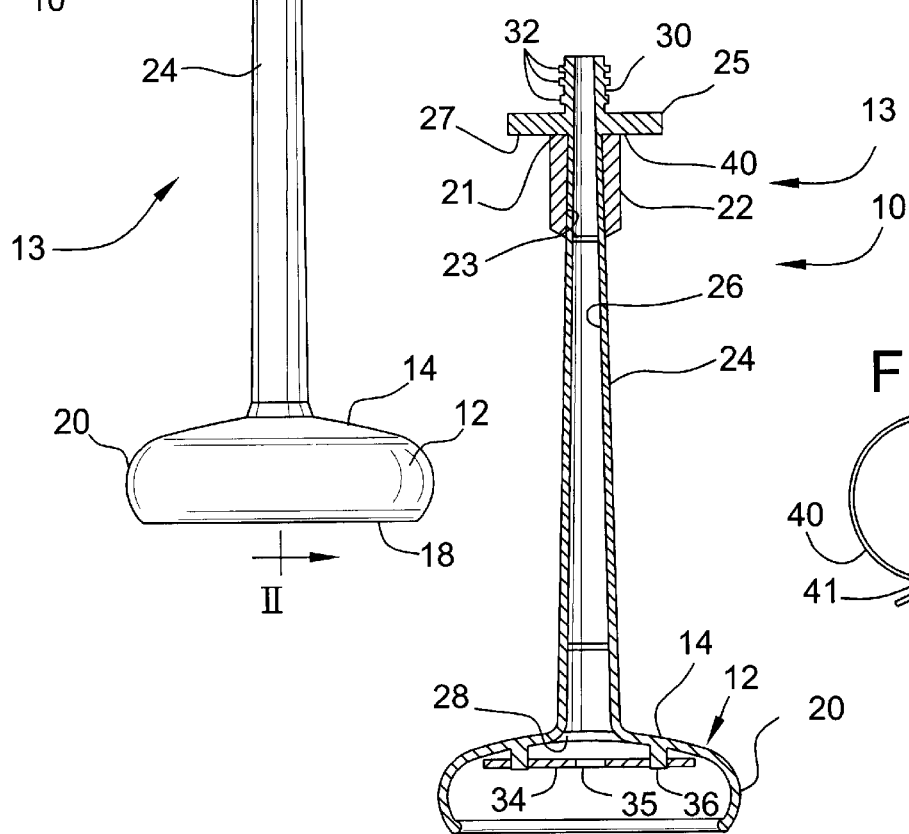
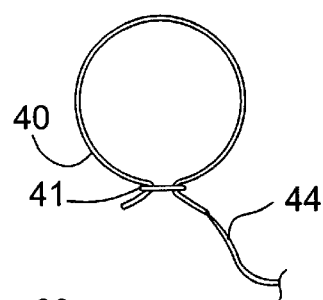
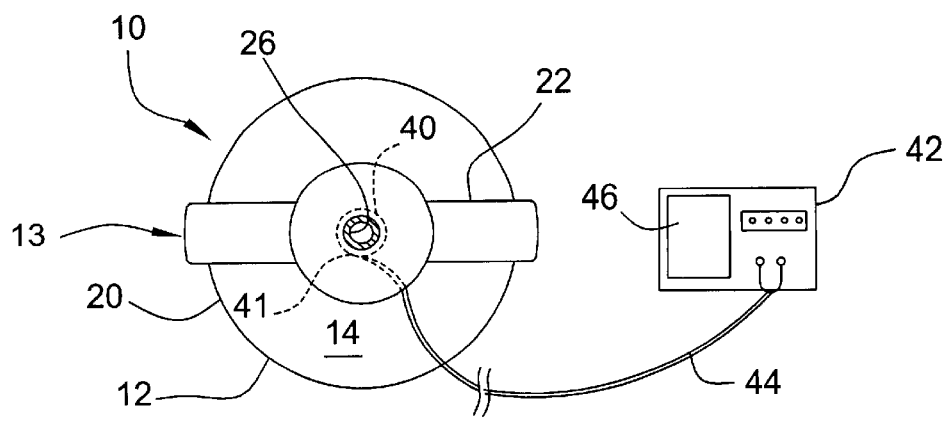

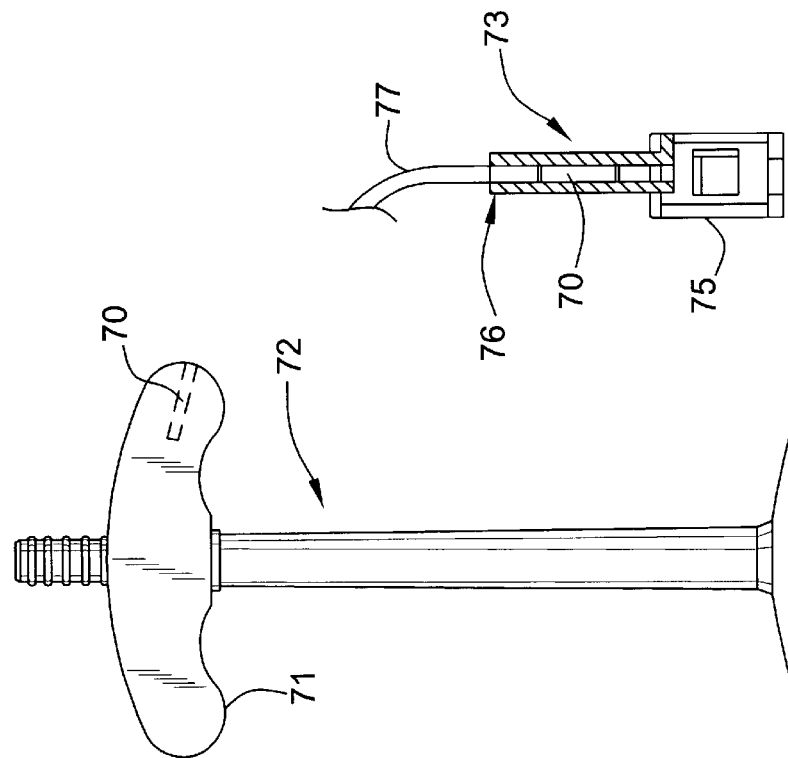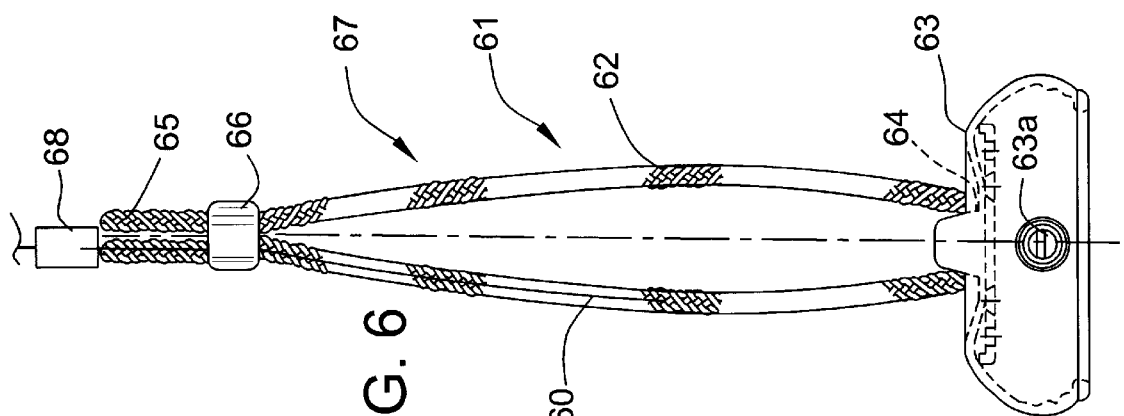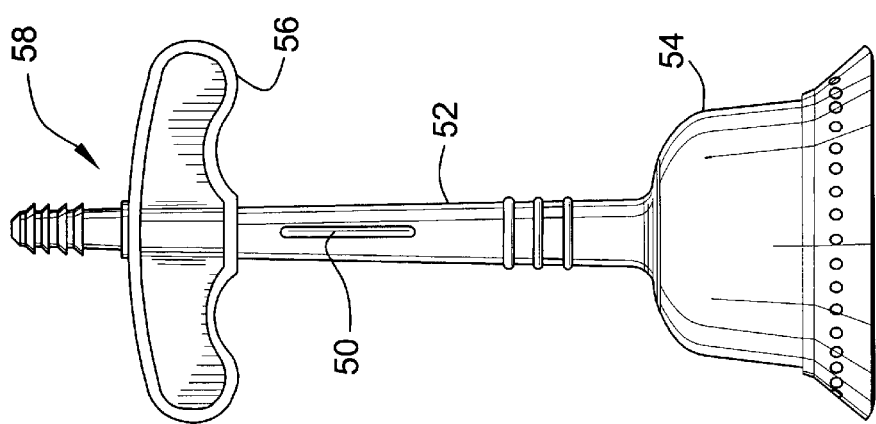

OBSTETRICAL VACUUM EXTRACTOR CUP WITH FORCE MEASURING CAPABILITIES

FIELD OF THE INVENTION

The present invention relates to an apparatus for facilitating the delivery of a child during childbirth, and more specifically relates to vacuum extractors for use during childbirth.

BACKGROUND OF THE INVENTION

Often, during childbirth, the birth mother cannot deliver the child without assistance from an attending physician. In some cases, all that is required is for the attending physician or other medical personnel to push down on the birth mother's upper abdomen when she bears down during delivery. While, in other cases, it is necessary for a physician to perform a cesarean section. However, for those cases which fall between those two extremes, some sort of intermediate assistance is often required. This typically entails the use of some type of medical device to aid the mother in the delivery of the child. In some circumstances, these devices may also be used to assist a physician during particularly difficult cesarean sections.

Forceps or other similar devices are one type of device which can be used by a physician to assist a mother during childbirth. Forceps, however, tend to be bulky and difficult for the physician to operate. Moreover, the use of forceps, at the very least, is uncomfortable for the mother and child and risks injury to both.

An alternative device which can be used to assist a mother during childbirth is a vacuum extractor. A vacuum extractor generally includes a cup, which is placed onto the child's head. A manipulation device of some sort is coupled to the cup. For example, an elongated hollow stem may be connected to the cup by which the cup may be positioned onto the child's head and through which vacuum pressure is introduced into the cup. Alternately, a chain or traction cord may be provided, and a vacuum introduced through a vacuum stem extending outward from the cup.

The introduction of vacuum pressure into the cup results in a suction force being applied between the cup and the child's head which adheres the cup to the child's head. Once the cup is positioned on and adhered to the head of the child, the vacuum extractor can then be used to extract the child from the birth canal by manipulating the traction cord, or some sort of handle or other gripping device coupled to the stem of the vacuum extractor. Several different types of vacuum extractors are known such as those described in U.S. Pat. Nos. 3,202,152, 5,019,086, 5,163,944 and 5,281,229 and U.S. application Ser. No. 08/853,422.

Although vacuum extractor devices are widely used, damage to maternal or fetal tissue may still result from improper operation and manipulation of the extractor. For example, the application of excessive traction force during extraction may result in such damage. Additionally, damage to the fetus may result from undesirable torsional forces being applied to the extractor during use.

Various methods have been used to measure forces applied during delivery in controlled settings. These arrangements, however, have typically required the use of an electric current. This passage of the electric current within the mother's body cavities is particularly troublesome in view of the fluids and mucous contained in areas such as the birth canal. Accordingly, the measuring devices have required a thorough sealing from the environment. Similarly, sanitation of such devices can be difficult, often requiring the use of additional sealing structures, such as external sleeves and the like. Further, electrical components so disposed within the body can interfere with the operation of other electrical devices necessary during delivery. As a result, such measuring devices are generally cumbersome and expensive to use, and have not typically been incorporated into commercial obstetrical vacuum extractors.

OBJECTS AND SUMMARY OF THE INVENTION

Accordingly, in view of the foregoing, it is a general object of the invention to provide a vacuum extractor which reduces the potential of injury to the fetal and maternal tissue. An additional object to is minimize the opportunity for injury to the fetus that may result from improper usage of a vacuum extractor.

It is a more particular object of the invention to provide an obstetrical vacuum extractor assembly which ultimately provides the physician with information to enable the physician to safely grasp and pull the head of the fetus without exceeding the desired tension or traction level.

Another object of the invention is to provide the physician with real time knowledge of the traction forces exerted on the fetal scalp thereby reducing the potential for the application of excessive force which can lead to injury to the child.

A further object of the invention is to provide an instrument that can be either easily sterilized for reuse or disposed of at a reasonable cost.

Another object of the present invention is to provide a vacuum extractor as characterized above which has a design that is economical to produce in that it can be manufactured in a cost efficient manner.

An additional object of the invention is to provide an obstetrical vacuum extractor that eliminates or minimizes the ability of the physician to apply a torsional force to the extractor during use.

The present invention provides these and other advantages and overcomes the drawbacks of the prior art by providing an obstetrical vacuum extractor for placement on a child's head for use during childbirth which provides measurements of the traction or tensile force applied to the head of the fetus. An optical strain gauge is coupled to the vacuum extractor to measure the strain resulting from the application of an extraction force. The measured strain is then transmitted and converted to a readout device which provides a readable indication of the force applied, the arrangement being calibrated to correlate the measured strain to the actual extraction force.

The optical strain gauge may be of any suitable design. For example, optical strain gauges, such as those marketed by Luna Innovations, Inc. of Blacksburg, Va., have been found to be particularly suitable. The conversion to a readable indication of the applied force may be made by any appropriate arrangement either before transmission to the readout device or at the readout device itself. Preferably, the optical strain gauge is in the form of optical sensor which is connected by an optical fiber to a read out device which analyzes the signal and displays the optical signal as an indication of force. Alternately, however, the measured strain may be converted to an electrical signal at a connector plug proximal to the vacuum extractor, the electrical signal then being transmitted to the readout device. Thus, the optical strain gauge utilizes light, rather than electricity, to measure strain. Accordingly, the vacuum extractor incorporating the optical strain gauge is much safer and easier to use, and may be more economically manufactured than such an extractor utilizing traditional force measuring technologies.

The vacuum extractor includes a vacuum cup of any known design having a side wall defining a hollow interior cavity. The side wall has a side wall edge that defines a cup opening and the vacuum cup further includes a vacuum opening in communication with the interior cavity of the cup which is adapted for connection to a vacuum source. A handle or other traction assembly is coupled to the vacuum cup to allow for manipulation of the extractor. Strain may be measured at substantially any position along the extractor where a tensile or compressive force results from the application of an extractor force. According to a preferred embodiment of the invention, the handle is coupled to the cup by an elongated hollow stem, the handle being slidably mounted on the stem and retained thereon by a flange. An optical sensor is disposed about the stem, between the flange and the handle such that the sensor measures the compressive force between the flange and the handle. The measured strain is then correlated to the extraction force applied to the device by the physician during use and displayed on a readout device. The optical strain gauge may be alternately disposed, for example, along the stem, where the stem stretches slightly, or the handle, where a bending or stretching occurs.

Additionally, the handle is preferably rotatably mounted on the stem, thus minimizing or eliminating the opportunity for the physician to apply torsional forces to the extractor during use.

These and other features and advantages of the invention will be more readily apparent upon reading the following description of a preferred exemplary embodiment of the invention and upon reference to the accompanying drawings wherein:

BRIEF DESCRIPTION OF THE DRAWINGS

FIG. 1 is a side elevational view of an illustrative obstetrical vacuum extractor constructed in accordance with teachings of the present invention.

FIG. 2 is a cross-sectional side view of the obstetrical vacuum extractor of FIG. 1 taken along line II—II.

FIG. 3 is a cross-sectional view of the obstetrical vacuum extractor of FIG. 1 taken along line III—III.

FIG. 4 is an enlarged plan view of the strain gauge of FIGS. 1–3 with the associated fastener and optical fiber.

FIG. 5 is a side elevational view of an obstetrical vacuum extractor of a second embodiment constructed in accordance with teachings of the invention.

FIG. 6 is a side elevational view of an obstetrical vacuum extractor of a third embodiment constructed in accordance with teachings of the invention.

FIG. 7 is a side elevational view of an obstetrical vacuum extractor of a fourth embodiment constructed in accordance with teachings of the invention.

FIG. 8 is an enlarged plan view of an anchor arrangement for the strain gauge of FIG. 7.

While the invention will be described and disclosed in connection with certain preferred embodiments and procedures, it is not intended to limit the invention to those specific embodiments. Rather it is intended to cover all such alternative embodiments and modifications as fall within the spirit and scope of the invention.

DETAILED DESCRIPTION OF THE PREFERRED EMBODIMENT

Referring now more particularly to FIG. 1 of the drawings, there is shown an illustrative obstetrical vacuum extractor 10 embodying the present invention which can be used in assisted child delivery techniques. The vacuum extractor 10 illustrated in FIGS. 1–3 comprises a hollow vacuum cup 12 having a base 14 and an annular side wall 20 which opens into a distal opening 18 for placement against the head of a child. The overall dimensions of the vacuum cup 12 are such that the vacuum cup 12 may be easily inserted into the birth canal and properly positioned onto the child's head.

While the invention will be described in connection with certain cup shapes, traction assembly, and extractor designs, it is not intended that the invention or the claims be limited to the enumerated structures. Of course, those skilled in the art will appreciate that the present invention is equally applicable to cups and extractor designs having other configurations. Further, the invention may be applied any cup design having any appropriate traction assembly.

To facilitate delivery, the obstetrical vacuum extractor 10 includes a traction assembly 13. In the embodiment illustrated in FIGS. 1–3, the traction assembly 13 is in the form of a handle 22, which is coupled to the cup 12 by an elongated stem 24. In order to establish a vacuum within the vacuum cup 12 and at the distal opening 18, the elongated stem 24 is hollow, or includes an interior bore 26 (see FIG. 2), which opens into the interior of the hollow vacuum cup 12 via a vacuum opening 28 in the cup 12. To facilitate coupling the hollow elongated stem 24 to a vacuum source (not shown), the outer surface of its proximal end 30 is provided with a series of ribs 32 which extend about the circumferential surface of the stem 24. It will thus be appreciated that when a suitable vacuum hose, such as flexible plastic tubing (not shown), is disposed about the proximal end 30 of the stem 20, the ribs 32 ensure an airtight connection with the vacuum hose.

To better distribute the applied vacuum within the cup 12, the vacuum extractor 10 may be provided with a disk 34 disposed a relatively short distance from the vacuum opening 28 into the interior of the hollow vacuum cup 12 as described in U.S. Pat. Nos. 5,163,944 and 5,281,299. The disk 34 is coupled to the base 14 of the cup 12 by a pair of pegs 36 (FIG. 2) which are received within openings of the disk 34 and then flattened by sonic welding, or the like to secure the disk 34 to the cup 12. The disk 34 includes a central opening 35 through which the vacuum communicates with the interior of the cup 12. Additionally, the periphery of the disk 34 is slightly smaller than the interior of the vacuum cup 12 such that the vacuum flow may also be distributed along the interior of the side wall 20 of the cup 12. Support ribs (not shown) along the interior of the cup 12 may be provided to assist in distributing the vacuum force.

Preferably, the hollow vacuum cup 12 and elongated stem 24 are unitarily molded from a substantially translucent, flexible plastic, such as polyethylene. Those skilled in the art will appreciate that the cup must be sufficiently flexible to be inserted into the birth canal and properly placed on the child's head, yet sufficiently rigid to withstand the vacuum developed within the bore 26 and cup 12. Typically, the vacuum pressure developed within the cup 12 during use ranges from about 15 to 23 inches Hg (approximately 39–59 cm Hg). Accordingly, the cup 12 must be molded of a sufficiently rigid material and the walls of the cup must be sufficiently thick to withstand the developed vacuum pressure. In one preferred embodiment, a low density polyethylene such as Dow Chemical #722 has been determined to be an appropriate material. Further, the extractor 10 must be sufficiently rigid to permit the physician to positively manipulate the extractor 10 during extraction.

In accordance with the invention, the vacuum extractor 10 may be utilized to measure the manipulation or extraction force applied to the extractor by the physician. In accomplishing this objective, an optical strain gauge is provided at a position on the extractor 10 where a force is developed or applied, or a deflection occurs. A strain gauge 40 preferably is provided along at least one of the handle 22 or the stem 24, or between the handle 22 and stem 24. It will be appreciated, however, that the strain gauge may be applied at a position on cup 12 where a deflection occurs.

According to a currently preferred embodiment of the invention illustrated in FIGS. 1–3, the strain gauge 40 is sandwiched between elements of the vacuum extractor 10 which are moveable relative to one another, in this case, the handle 22 is moveable relative to the stem 24 of the vacuum extractor 10. The handle 22 has a bore 23, which receives the stem 24. In order to retain the handle 22 on the stem 24, an enlarged, generally radially-extending flange 25 is provided. As may be best seen in FIG. 2, the handle 22 is disposed subjacent the flange 25 so that the flange 25 prevents the handle 22 from being pulled from the vacuum extractor 10 during use. It will be appreciated by those skilled in the art that the moveable coupling of the handle relative to the cup likewise effectively prevents the physician from placing a rotational torque on the vacuum extractor 10 and, accordingly, the infant's head during delivery. This minimizes the opportunity for certain types of injuries to the infant during delivery.

In this embodiment, the strain gauge 40 is disposed between the proximal surface 21 of the handle 22 and the distal surface 27 of the flange 25. Preferably, the strain gauge 40 is generally in the shape of an omega (Ω), as shown in FIGS. 3 and 4, which fits around the stem 24 of the extractor 10. The strain gauge 40 may be held in position by a clip, snap, or other fastener 41. In this way, during use, the gauge 40 measures the strain resulting from the force applied between the handle 24 and the flange 25 as the physician applies a force to the extractor 10 during the birthing process. The strain gauge 40 is preferably in the form of a fiber, and is coupled to a transmitting/receiving device 42 by way of an optical fiber 44.

The transmitting/receiving device 42 may be of any commercially available system that is capable of transmitting an optical signal and receiving a reflective optical signal. In the embodiment illustrated, a device for analyzing and displaying reflected optical signals 46 is shown integrally with the transmitting/receiving device 42. The device for analyzing and displaying reflected optical signals 46 may likewise be any appropriate device already known in the art, or separate devices may be provided for analyzing the data and for displaying a readable indication of the force applied. It will be appreciated that one of ordinary skill in structural analysis techniques may readily utilize appropriate commercially available equipment for these functions.

According to an important feature of the invention, the optical gauge for sensing strain need only measure the tensile forces, not the torsional or bending forces. It has been determined that it is not necessary to measure the compressive forces provided the tensile or tractive forces are maintained below a predetermined level. It will be appreciated by those skilled in the art that the use of only tensile sensing strain gauges, as opposed to a plurality of strain gauges sensing both tensile forces and flexural or bending forces, greatly simplifies not only the fabrication of the vacuum extractor 10, but the calibration of the device.

It will be appreciated that the strain gauge 40 may be alternately positioned on the vacuum extractor 10, so long as it is capable of measuring the tensile or tractive forces placed on the device 10. In the embodiment illustrated in FIG. 5, a strain gauge 50 is disposed along the stem 52 coupling the cup 54 to the handle 56 of the vacuum extractor 58. The strain gauge 50 is rigidly coupled to the stem 52 such that even minor "stretching" of the stem 52 may be measured by the strain gauge 50. For example, the strain gauge 50 may be attached to the stem 52 by an adhesive, such as an appropriate glue, or by molding the strain gauge 50 into the stem 52.

In the embodiment illustrated in FIG. 6, the traction assembly 61 is in the form of a traction cord 62 which is coupled to the vacuum cup 63 through an opening 64 along the cup 63. It will be noted that the cup 63 has an opening 63a for attachment to a vacuum source. To facilitate the application of a tractive force by the physician, the ends 65 of the traction cord 62 are coupled together by a clip 66. Similar to the embodiment illustrated in FIG. 5, in the embodiment illustrated in FIG. 6, a strain gauge 60 may be coupled to the traction cord 62 to measure the tractive force applied by the physician. The fiber optic strain gauge 60 may be applied to the cable 62 with a connector, or the strain gauge 60 may be inserted inside of the cable 62 itself. In either case, the cable 62 preferably includes a reinforced wall portion to ensure the proper measurement of the applied force.

While a fiber optic cable may be provided to transmit the signal from the strain gauge 60 to an analyzing and readout device, as was utilized in the embodiment illustrated in FIGS. 1–3, the data from the fiber optic strain gauge 60 may be analyzed more proximally to the vacuum extractor 67, and then transmitted onward to a display device. In the embodiment illustrated in FIG. 6, a connector plug 68 is provided which converts the measured optical strain data into an electrical signal. The signal is then passed on to a readout device (not illustrated) which displays an indication of the level of force applied to the extractor 67.

In yet another embodiment, as illustrated in FIG. 7, a strain gauge 70 is coupled directly to the handle 71 of a vacuum extractor 72 to measure the deflection or deformation of the handle 71. The strain gauge 70 may be molded into the handle 71, or may be threaded into an anchor-type arrangement as a part of an assembly 73 which is inserted into a bore 74 in the handle 71 as illustrated in FIG. 8. The fiber optic sensor 70 preferably is threaded into an anchor 75 which is received into the bore 74 in the handle 71. The optical fiber 70 is coupled to a transmitting/receiving device 32 by way of a tension spacer 76 and an optical fiber 77.

In summary, the optical strain gauge may be disposed at any appropriate position in or along the vacuum extractor so long as it is arranged to measure the tension or deformation of the extractor at that point. The optical signal may be transmitted directly to a analyzer/display device(s) or the optical signal may be converted to an electrical signal which is transmitted on to a display device. Thus, calibrating the analyzer or converter to the strain gauge, the physician may obtain a measurement of the force applied to the infant by measuring the deflection of the vacuum extractor. The force measuring method may be utilized with substantially any vacuum extractor design, so long as the strain gauge is appropriately placed to measure the tension or deflection of the extractor.

All of the references cited herein, including patents, patent applications and publications, are hereby incorporated in their entireties by reference.

While this invention has been described with an emphasis upon preferred embodiments, it will be obvious to those of ordinary skill in the art that variations of the preferred embodiments may be used and that it is intended that the invention may be practiced otherwise than as specifically described herein. Accordingly, this invention includes all modifications encompassed within the spirit and the scope of the invention.

We claim as our invention:

1. An obstetrical vacuum extractor comprising
   a vacuum cup having a base and an annular side wall opening into a distal opening, the vacuum cup being adapted for connection to a vacuum source for creating a vacuum within the cup,
   an elongated traction assembly coupled to the cup, and
   a optical strain gauge coupled to at least one of the cup or traction assembly whereby the strain gauge measures strain associated with an extraction force exerted on the vacuum extractor.

2. The obstetrical vacuum extractor of claim 1 wherein the traction assembly comprises an elongated stem having a flange extending axially therefrom, the traction assembly further comprising a handle having a bore, the handle being disposed subjacent the flange, and the bore being disposed about the stem, the strain gauge being disposed between the flange and the handle.

3. The obstetrical vacuum extractor of claim 1 wherein the traction assembly comprises an elongated stem and a handle having a bore, the stem being received in the handle bore such that the handle is rotatable relative to the stem.

4. The obstetrical vacuum extractor of claim 1 wherein the traction assembly comprises an elongated stem, the strain gauge being coupled to the elongated stem.

5. The obstetrical vacuum extractor of claim 4 wherein the strain gauge is adhered to the stem.

6. The obstetrical vacuum extractor of claim 4 wherein the strain gauge is molded to the stem.

7. The obstetrical vacuum extractor of claim 1 wherein the traction assembly comprises a handle, the strain gauge being coupled to the handle.

8. The obstetrical vacuum extractor of claim 7 wherein the handle comprises a bore, and the strain gauge is disposed within the bore.

9. The obstetrical vacuum extractor of claim 7 wherein the strain gauge is molded within the handle.

10. The obstetrical vacuum extractor of claim 1 wherein the traction assembly comprises a traction cord, the strain gauge being coupled to the traction cord.

11. The obstetrical vacuum extractor of claim 10 wherein the strain gauge is adhered to the traction cord.

12. The obstetrical vacuum extractor of claim 1 wherein the strain gauge is an optical strain gauge.

13. The obstetrical vacuum extractor of claim 1 further comprising a readout device coupled to the strain gauge.

14. The obstetrical vacuum extractor of claim 13 further comprising a converter coupled to the strain gauge and the readout device whereby the reading from the strain gauge is converted into an electrical signal and transmitted to the readout device.

15. The obstetrical vacuum extractor of claim 13 wherein the extractor further comprises an optical fiber coupling the strain gauge to the readout device.

16. A method of monitoring the extraction force applied to a target bodily tissue during the use of a vacuum extractor, the method comprising the steps of
   applying a distal opening of a vacuum cup to the target tissue,
   supplying a vacuum to the interior of the vacuum cup,
   applying an extraction force to an elongated traction assembly coupled to the vacuum cup, and
   measuring the strain developed along a portion of vacuum cup and/or the elongated traction assembly as a result of the application of the extraction force using a strain gauge coupled to at least one of the vacuum cup and/or the elongated traction assembly using an optical strain gauge.

17. The method of claim 16 further comprising the step of transmitting a strain reading to a readable display device.

18. The method of claim 17 further comprising the step of calibrating the readable display device to display a force associated with the strain reading.

19. The method of claim 16 wherein the target bodily tissue is the scalp of a fetus.

20. The method of claim 16 further comprising the steps of converting the strain reading to an electrical signal, and transmitting the electrical signal to a readable display device.

21. The method of claim 16 further comprises the steps of transmitting an optical strain signal via an optical fiber and displaying a correlated signal on a readable display device.

* * * * *